United States Patent [19]
Beale

[11] Patent Number: 6,008,252
[45] Date of Patent: *Dec. 28, 1999

[54] METHOD FOR INCREASING MUSCLE MASS IN A MAMMAL

[76] Inventor: Paxton K. Beale, 1801 Bush St, Ste 300, San Francisco, Calif. 94109

[ * ] Notice: This patent is subject to a terminal disclaimer.

[21] Appl. No.: 09/071,008

[22] Filed: May 1, 1998

Related U.S. Application Data

[60] Continuation-in-part of application No. 08/686,820, Jul. 26, 1996, Pat. No. 5,756,469, which is a division of application No. 08/686,819, Jul. 26, 1996, Pat. No. 5,716,926.

[51] Int. Cl.⁶ .................................................... A01N 37/12
[52] U.S. Cl. ........................................... 514/563; 557/625
[58] Field of Search .................................... 514/563, 557, 514/625

[56] References Cited

U.S. PATENT DOCUMENTS

| | | | |
|---|---|---|---|
| 4,215,197 | 7/1980 | Tarbutton | 435/18 |
| 5,256,697 | 10/1993 | Miller et al. | 514/625 |
| 5,283,260 | 2/1994 | Miller et al. | 514/563 |
| 5,716,926 | 2/1998 | Beale et al. | 514/2 |
| 5,756,469 | 5/1998 | Beale | 514/23 |
| 5,817,329 | 10/1998 | Gardiner | 424/439 |

*Primary Examiner*—Kevin E. Weddington
*Attorney, Agent, or Firm*—Donald O. Nickey; Standley & Gilcrest LLP

[57] ABSTRACT

The present invention is based in part upon the discovery that the use of pyruvate in enteral formulations, in combination with anaerobic exercise produces a synergistic effect in increasing the amount of lean body mass or muscle tissue in a mammal. The present invention relates generally to a composition for enhancing the protein concentration or muscle mass of a mammal and a method for enhancing the protein concentration or muscle mass in a mammal. More specifically, the present invention relates to the consumption of a composition which comprises calcium pyruvate and potassium pyruvate and derivatives of pyruvate such as pyruvyl-creatine and anaerobic exercise to enhance muscle mass. The method of the present invention comprises administering to a mammal in need of enhancing its protein concentration or muscle mass, a composition comprising pyruvate and the subjecting of a mammal to anaerobic exercise. The pyruvate composition can take the form of powders, liquids, pills, capsules, tablets, food additives, candies or confections.

24 Claims, No Drawings

METHOD FOR INCREASING MUSCLE MASS IN A MAMMAL

RELATED APPLICATIONS

This application is a continuation-in-part of U.S. patent application Ser. No. 08/686,820 filed Jul. 26, 1996, now U.S. Pat. No. 5,756,469 which is a divisional application of U.S. Ser. No. 08/686,819 filed Jul. 26, 1996, now U.S. Pat. No. 5,716,926 issued Feb. 10, 1998.

TECHNICAL FIELD

The parent application related generally to a composition for and method of enhancing the protein concentration or muscle mass of a mammal. The parent applications disclosed a composition which comprises pyruvate and/or derivatives of pyruvate and a novel blend of proteins and/or amino acids that possesses an amino acid profile that is similar to the amino acid profile of human muscle tissue. The method of the present invention comprises the steps of administering to a mammal in need of enhancing its muscle mass, a composition comprising pyruvate and thereafter or prior thereto, having the mammal engage in at least twenty (20) minutes of anaerobic exercise. The method of this invention results in a surprising increase of muscle mass. Most preferably, the source of pyruvate contains little or no sodium.

BACKGROUND ART

Athletes engage in strenuous training to accomplish the goals of their sport. This strenuous training essentially amounts to trauma to the body, in that the human body interprets every strenuous work-out as a threat to its survival. It is known that muscle damage, caused by excessive training, releases the catabolic hormone prostaglandin-E2. Strenuous exercise also causes the release of adrenocorticotropin (ACTH), which is a pituitary hormone. The presence of increased levels of ACTH increases the production of the catabolic hormone cortisol. Cortisol is also known as hydrocortisone, which is a glucocorticoid of the adrenal cortex that is a derivative of cortisone which is used in the treatment of rheumatoid arthritis. Thus, cortisol is a naturally occurring anti-inflammatory steroid. This catabolic hormone results in the release of amino acids from muscle tissue and prevents absorption of glucose. Cortisol, as a catabolic stress hormone, cannibalizes muscle tissue. High cortisol levels also result in the breakdown of connective tissue, lowered immunity and reduced muscle RNA synthesis. While cortisol may be a detriment to the athlete, scientists have conjectured that when the human body is stressed or traumatized, it triggers a "fight or flight" survival response. The biological design of cortisol is such that when a human is threatened, cortisol levels rise and mobilize the body for action by breaking down fat and muscle stores for emergency energy. Cortisol also reduces swelling in the event of injury. After the threat or trauma has subsided cortisol levels return to normal. The cortisol-stress relationship is designed for intermittent physical threats and not the constant stimulation provided by today's aggressive athletes. Ongoing training results in cortisol levels that do not return to normal for extended periods of time and thereby result in the breakdown or loss of muscle tissue.

After strenuous exercise, muscle tissue enters a stage of rapid nitrogen absorption in the form of amino acids and small peptides in order to rebuild the muscle fibers, grow and add new muscle fibers. During this period of repair and growth, it is important that the muscle cells have available to them sufficient levels of nitrogen in the form of amino acids.

Exercise is the repeated use or activity of a muscle group or organ. Exercise is bodily exertion for the sake of developing and maintaining physical fitness. Anaerobic exercise occurs when the activity results in the body incurring an oxygen debt. In contrast, aerobic exercise is physical conditioning involving exercise that does not cause an oxygen debt, such as distance running, jogging, walking, swimming, circuit training or cross country skiing strenuously performed so as to cause a marked, but steady increase in respiration and heart rate over an extended period of time. The most familiar form of anaerobic exercise is weightlifting; but handball, football and tennis are other examples.

Athletes that overtrain sometimes enter into a catabolic state. Muscle catabolism occurs when the athlete enters a negative nitrogen balance. People on diets usually have a negative nitrogen balance and therefore lose muscle tissue when they lose weight. In contrast, a positive nitrogen balance means the animal has enough nitrogen left over to synthesize muscle proteins.

The caloric requirements of a mammal are dependent upon the energy expenditure of the mammal. A hypocaloric diet is one that is under or less than the energy expenditure of the mammal. The typical weight loss diet is hypocaloric, thus the body will use energy stores such as fat and muscle tissue to make up the difference between the energy content of the diet and the energy expended. Thus, the animal will lose weight. In contrast, a hypercaloric diet will supply an amount of energy beyond that required for a given level of activity. In such a situation, the body will store the excess energy in the form of fat and/or muscle tissue. In the usual circumstances, the excess energy will be deposited as adipose tissue or fat.

The present invention is based in part, upon the discovery that the use of pyruvate in combination with anaerobic exercise, produces a synergistic effect in increasing the muscle tissue of a mammal while at the same time increasing the metabolism of fat in the body.

As used herein and the claims, the term "pyruvate" means any salt or ester of pyruvic acid. Pyruvic acid has the formula:

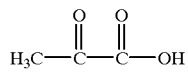

Pyruvic acid is a colorless liquid with an odor resembling that of acetic acid and has a melting point of 13° C. Pyruvic acid is an intermediate in the breakdown of sugars to alcohol by yeast. The mineral salts of pyruvic acid, such as magnesium pyruvate, potassium pyruvate or calcium pyruvate or mixtures thereof are useful in the present invention. Sodium pyruvate is not especially preferred as it is known that sodium is associated with various negative medical conditions such as high blood pressure, water retention and heart disease. Further, certain athletes, such as bodybuilders, desire to present a defined visual image of their body which shows muscle definition and thus, the water retention properties of the sodium salt are not beneficial. Pyruvate precursors in the form of pyruvamides or pyruvyl-amino acids are also useful in the present invention. Pyruvyl-glycine is representative of the useful pyruvyl-amino acids. Another form of pyruvate precursor is pyruvyl-creatine, wherein pyruvate is bonded to creatine either covalently or ionically. Creatine or methylguanidineacetic acid has the chemical formula:

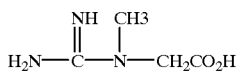

and is present in the muscle tissue of vertebrates. It plays an important part in the cycle of chemical changes involving muscular contraction. Normally, creatine is the form in which creatine is excreted. Creatine is formed in the body by the methylation (by methionine) of glycocyamine.

Pyruvate has a number of known useful applications in medicine. Pyruvate in combination with other compounds has been described for retarding fatty deposits in livers (U.S. Pat No. 4,158,057); for treating diabetes (U.S. Pat. No. 4,874,790); for retarding weight gain (U.S. Pat. Nos. 4,812, 879, 4,548,937, and 4,351,835); to increase body protein concentrations in a mammal through decreasing the deposition of fat (U.S. Pat. No. 4,415,576); for treating cardiac patients to increase the cardiac output without accompanying increase in cardiac oxygen demand (U.S. Pat. No. 5,294,641); for extending athletic endurance (U.S. Pat. No. 4,315,835); for retarding cholesterol increase (U.S. Pat. No. 5,134,162); for inhibiting growth and spread of malignancy and retarding DNA breaks (U.S. Pat. No. 5,612,374) and for inhibiting generation of free radicals (U.S. Pat. No. 5,480, 909). All of these references are incorporated herein by reference.

U.S. Pat. No. 4,981,687 relates to compositions and methods for achieving improved physiological response to exercise. More specifically, this patent discloses a beverage comprising water, sugar, electrolytes, glycerol and pyruvate; and its use to ameliorate the effects of physical exertion. The teachings of U.S. Pat. No. 4,981,687 are incorporated herein by reference.

U.S. Pat. No. 5,089,477 discloses the use of pyruvate in a liquid composition that is used to prevent weight loss in agricultural animals resulting from dehydration.

U.S. Pat. No. 5,147,650 and U.S. Pat. No. 5,238,684 discloses and claims a fluid composition comprising water, electrolytes, sugar, glycerol, lactate and pyruvate. The teachings of U.S. Pat. Nos. 5,147,650 and 5,238,684 are incorporated herein by reference.

U.S. Pat. No. 5,236,712 discloses and claims a beverage containing water, electrolytes, pyruvate and alanine in a concentration of from about 0.5% to about 10%. The teachings of U.S. Pat. No. 5,236,712 are incorporated herein by reference.

Pyruvate in various forms has been proposed for enteral administration and for parenteral administration. Typically, pyruvates are available in the form of salts, for example, calcium pyruvate and sodium pyruvate. U.S. Pat. Nos. 5,283,260 and 5,256,697 disclose uses for the pyruvyl-amino acids and methods for their production.

Pyruvate has been administered to mammals enterally or parenterally typically at superphysiological levels. The amount of pyruvate administered generally ranges from 0.5 to 20% of the mammal's daily caloric intake. For a 2,000 calorie diet, this would range from 2.5–100 grams per day of pyruvate. For enteral consumption, the pyruvate may be disbursed or dissolved in a beverage product or may be included in cookies, candies or other foods. Pyruvate may also be introduced as an aqueous solution parenterally.

Protein supplementation for serious athletes, such as body builders, is well accepted and is well known to increase the muscle mass of the athlete. Typically recommended dosages range between 2.0 and 3.5 gms of quality protein per kilogram of body weight per day. Numerous sources for the protein supplements are known, such as milk, egg, soy, beef and vegetable protein. Isolated fractions of these sources are also known such as ion-exchange whey protein, caseinates, whey protein concentrates, immunoglobulin and egg albumin. Protein supplements typically are provided as powders. It is also known to provide protein supplementation in the form of peptides (hydrolyzed protein) or even free amino acids. These approaches have two major limitations; cost and taste.

There are more than 600 skeletal muscles in the body. Skeletal muscles are also called "voluntary muscles" because they are responsible for purposeful movement of the body such as running and jumping. The brain sends signals to each and every skeletal muscle fiber enabling us to perform actions when we wish to do them.

There are three (3) different types of muscle in the body: skeletal muscle, smooth muscle and cardiac muscle. All three types of muscle are composed of fibers that permit movement through coordinated contraction and relaxation. At the microscopic level, the three types of muscle share a common mechanism for contracting. The basic working elements are actin and myosin filaments. When a muscle contracts, the individual myosin filaments slide over the actin filaments, much like an extendable ladder does when it closes. This causes the overall length of the muscle to shorten. One surprising aspect of the present invention is that a special mixture of potassium and calcium salts of pyruvate can be effective in increasing the muscle mass in a mammal when consumed in conjunction with anaerobic exercise.

In view of the present disclosure or through the practice of the present invention, other advantages or solutions to other problems will become apparent.

DISCLOSURE OF THE INVENTION

While the use of pyruvate is known for various medical indications, the prior art has failed to recognize or even consider the combination of certain forms of pyruvate in relatively low doses with anaerobic exercise to achieve substantial gains in muscle mass (sometimes referred to as increases in protein concentration) in the body of a mammal. This effect is not believed to be due to the reduction in fat deposition properties of pyruvate since the presently observed phenomenon occurs well below the dosage recited in the prior art for reduction in fat deposition. In a preferred embodiment, the consumption of calcium pyruvate and potassium pyruvate will result in a surprising increase in muscle mass when combined with at least twenty (20) minutes of anaerobic exercise per day. Even more surprising are the synergistic results that can be achieved when calcium and/or potassium pyruvate is combined with the pyruvate precursor pyruvyl-creatine. Further, the use of pyruvyl-creatine only will also produce a significant increase in muscle tissue. An additional aspect of the present invention is that the anaerobic exercise in combination with from 1.6–10 grams per day of pyruvate can result in significant weight gain through the increased production of muscle tissue. The prior art has not disclosed nor suggested the methods of the present invention.

There is disclosed a method for increasing the muscle mass of a mammal, said method comprising the steps of 1) administering pyruvate to said mammal, and 2) anaerobically exercising said mammal. In a more preferred embodiment, the pyruvate is administered in a form selected from a) a salt selected from the group consisting of calcium, potassium and magnesium; 2) a pyruvate precursor; and 3) mixtures thereof. In a yet more preferred embodiment, the pyruvate is administered as a mixture of calcium pyruvate and potassium pyruvate. The most preferred pyruvate source is a mixture of calcium pyruvate, potassium pyruvate and pyruvyl-creatine. In a further embodiment, pyruvyl-creatine alone is administered to the mammal. The weight ratio of calcium pyruvate to potassium pyruvate can range from 1:10 to 10:1 with about 1:1 being most preferred. The weight ratio of pyruvyl-creatine to the sum of all other sources of pyruvate can range from 1:1 to 10:1, with about 5:1 being most preferred.

The amount of anaerobic exercise should be at least twenty (20) minutes per day with at least thirty (30) minutes per day being more preferred and at least forty-five (45) minutes per day being most preferred. The form of anaerobic activity is not critical so long as the exercise results in the body achieving an oxygen deficit. The most preferred form of anaerobic exercise is weightlifting.

The dosage of pyruvate should result in the consumption of at least 1.6 rams of pyruvic acid per day. One skilled in the art will appreciate that depending upon the form of the pyruvate. i.e., sodium pyruvate or calcium pyruvate, the amount of the pyruvate anion per source will vary For example, calcium pyruvate (Ca $(CH_3COOCOO)_2$) has a molecular weight of 214 or which 40 is the calcium. Thus, 1 gram of calcium pyruvate contains about 190 mgs of calcium and about 810 mgs of pyruvic anion. Therefore, to obtain at least 1.6 grams of pyruvic anion, the mammal should consume about 2.0 grams of calcium pyruvate. With this understanding, one skilled in the art can readily determine what amount of a given source of pyruvate must be consumed to accomplish the method of this invention.

The inventor has discovered that consumption of about 1.6 to about 10.0 rams per day of pyruvic anion, in combination with anaerobic exercise will result in outstanding muscle mass increase when the mammal consumes a hypercaloric diet. The caloric intake per day should exceed, by a modest amount (i.e., 5–10%) the energy expenditure per day. For example, an average human male with a body weight of about 80 kgs will require at least 2,000 calories per day if he engages in at least 20 minutes of anaerobic exercise per day. Those skilled in the art will readily be able to calculate the number of calories per day for a given individual.

One aspect of the invention is based upon the discovery that relatively low doses of pyruvate (1.6–10 grams per day) is extremely effective in promoting the growth of muscle tissue in a mammal when combined with a hypercalorie diet and anaerobic exercise.

There is further disclosed a method for increasing the lean body mass or muscle mass of a mammal, said process comprising the steps of: a) administering to a mammal in need of increased lean body mass or muscle mass, a composition comprising pyruvate: and b) engaging the mammal in anaerobic exercise.

There are two main types of muscle fibers—red (or slow twitch) and white (or fast twitch) with a third type displaying intermediate characteristics of the two. Slow twitch fibers rely on oxygen to perform aerobic work. They are relatively weak fibers but can contract repeatedly for long periods of time. Fast twitch fibers, on the other hand, are suited for high powered, mainly anaerobic, work. They are capable of generating very high forces, but fatigue readily. Thus, one further aspect of this invention is directed to the discovery that the compositions disclosed herein are especially suited for the fast twitch fibers. Thus, the consumption of calcium and potassium pyruvate appears to favor the fast twitch excitation of the muscle. This is important because fast twitch muscle fibers possess the greatest potential for growth from exercise. As noted in the Examples discussed below, the consumption of calcium and potassium pyruvate, in conjunction with anaerobic exercise, is more effective at inducing muscle growth than exercise without the consumption of the pyruvate salts. Further, as discussed below, the consumption of the pyruvate salts allows additional exercise to be conducted and thereby placing a greater metabolic demand on the body. This means that metabolic processes are stimulated that have beneficial, indirect effects on muscle growth and body fat loss. Such effects are achieved by the stimulation of metabolic hormones that regulate body composition; for example, growth hormone testosterone and insulin-like growth factor 1.

These hormones play a dramatic role in how the body responds to exercise, i.e. increasing the amount of muscle tissue.

Specific forms of pyruvate useful in the present invention include magnesium pyruvate, calcium pyruvate, potassium pyruvate, pyruvyl-glycine, pyruvamines, pyruvyl-alanine, pyruvyl-leucine, pyruvyl-tyrosine, pyruvyl-glutamine, pyruvyl-valine, pyruvyl-isoleucine, pyruvyl-phenylalanine, pyruvyl-proline, pyruvyl-creatine, pyruvyl-sarcosine, their amides, esters and salts, and mixtures thereof. Especially preferred is a mixture of calcium pyruvate and potassium pyruvate. Most preferred is a mixture of pyruvyl-creatine, potassium pyruvate and calcium pyruvate.

The pyruvate may be combined with other materials such as fats, carbohydrates, vitamins, minerals, sweeteners, flavoring agents and the like. For example, the preferred mixtures may be combined with known food ingredients or dispersed in a liquid such as orange juice, and consumed orally.

In the method of the present invention, the mammal, preferably a human, consumes at least 1.6 gms per day of pyruvate anion. The preferred range is 1.6–10 grams per day. On a percent of calories basis, using a 2,000 calorie standard, the pyruvate can comprise from 0.3 to about 2.0% of total caloric intake.

The method of the present invention contemplates the daily oral administration of the pyruvate and a daily or every other day anaerobic workout. Dosages of the pyruvate can occur prior to and/or subsequent to the anaerobic exercise.

In order to demonstrate the present invention, the following examples are submitted.

EXAMPLE I

Preparation of the Pyruvate Composition

One aspect of the present invention resides in the novel blend of potassium and calcium pyruvate. This blend of potassium and calcium salts provides the subject desiring to increase its muscle mass with the proper level and ratio of these elements. The sodium salt of pyruvic acid should be avoided as it is more hydroscopic than the potassium, calcium and magnesium salts. Potassium salts are consumed by bodybuilders prior to a contest to "pump up" their muscles since potassium holds water in the muscle. In contrast, sodium is known to increase water content of the muscle cell and between the muscle cells. This water between the cells is unacceptable as it gives the bodybuilder a "flattened out" look as opposed to improved definition of muscle groups.

In similar fashion, the consumption of pyruvyl-creatine is preferred in the method of this invention as creatine is known to increase the water content of muscle cells.

Thus, to provide a preferred mixture of pyruvate for use in the method of this invention. 40 kilograms of calcium pyruvate in powder form is combined with 60 kg of potassium pyruvate in powder form and blended in a "V"-mixer for 10 minutes. 100 kgs of pyruvyl-creatine in powder form is then added to the mixer and mixing is continued for an additional 15 minutes. I kg of a PVC as a pelletizing agent is then added to the mixer and mixing is continued for 15 minutes. The mixture is then placed in a tablet press and 1.0 gram tablets are prepared.

EXAMPLE II

Clinical Evaluation

Three groups of five (5) healthy human males (Control, Pyruvate and Control Placebo). with an average age of thirty-five (35) years, are enrolled in the study after informed written consent is obtained. The body mass index (BMI) is determined for each subject by dividing bodyweight (Kg) by the square of height (m) as described in Broy. Ann. N.Y. Acad. Sci. 499: 14–27, 1987. Subjects with a BMI of less than 25 are excluded from the study as are subjects that are using weight loss products or suffering from any illness or disease.

The study is 10 weeks in length and each subject consumes a diet consisting of 2,000 calories ±100 calories per day in conformance with a recommendation of a dietitian. Each subject is provided a detailed food diary for tracking food consumption. The Control group received no pyruvate or placebo, but did engage in sixty (60) minutes of anaerobic exercise as set forth below. The anaerobic exercise program is the same for each study group and consisted of bench presses, clean, squats, curls, military presses and the like at weights and repetitions determined by an exercise physiologist (i.e., typically 6–12 repetitions or until maximum failure) to accomplish the anaerobic exercise within sixty minutes. More specifically, using standard muscle physiology on, for example, a given Monday and Thursday, the subjects work the back muscles, followed by the deltoids, triceps and biceps. On Tuesday and Fridays, the subjects work the quadriceps, hams, calves and chest muscle groups. A minimum of six (6) sets per muscle group is accomplished.

The Pyruvate group consumed nine (9) tablets (3 tablets, 3 times per day) per day as prepared in Example I. The Placebo group consumed 9 tablets per day of a maltodextrine/salt mixture to mimic the caloric density and the calcium and potassium levels of the pyruvate tablets.

Data on diet consumption per day is collected and the subjects are also weighed daily.

On days 0, 7, 21, 39, 60 and 70, the subjects are evaluated for total body water using the bioelectric impedence analysis (BIA) as known to those skilled in the art.

Subjects are also tested on days 0, 21 and 70 for % body compositional make up to determine the % of lean body mass (LBM) or muscle mass in the subject. The data will indicate that the Pyruvate group has a 15% greater increase in lean body tissue (muscle) over Control and Placebo. The study will also demonstrate that the strength of the Pyruvate group, as evidenced by increases in total weight lifted, will increase at least 20% more than Control or Placebo.

There will be found a marked increase in the amount of muscle tissue in the subjects fed the composition of the present invention. The synergistic effect of pyruvate and anaerobic exercise provides for a significant increase in muscle tissue. The mixture of calcium pyruvate and potassium pyruvate also provides an improved balance of electrolytes which also improves the physical appearance of the bodybuilder.

An additional important indicator of the novel composition's effectiveness has been a significant lowering of the perceived difficulty of long term exercise among individuals that consume the calcium pyruvate and potassium pyruvate mixture. The lower difficulty perceived by individuals receiving the pyruvate composition of the invention will lead to enhanced physical performance, especially when long term exercise is involved.

EXAMPLE III

Calcium Pyruvate 22 pigs of 10 weeks of age are individually housed in fiberglass pens and are randomly assigned to a Control or a Pyruvate Diet. The Control diet consists of a standard swine feed while the Pyruvate diet consists of the standard swine feed plus calcium pyruvate at levels of 2% of the calories. At the beginning of the experiment, the animals are weighed and ultrasound measurements are made over the ribs of the animals to determine fat thickness. Feed consumption is measured and at the end of the 5 week study period the animals are weighed and ultrasound measurements of fat thickness are taken. This use of ultrasound to measure fat deposition has been shown to be a reliable method of assessing these values without slaughtering the animal.

The data will indicate that the animals all gained about the same amount of weight, however, the pigs consuming the diet containing pyruvate evidenced a 30% increase in muscle tissue as evidenced by the ultrasound fat measurements. Thus, the consumption of calcium pyruvate at a level of 2% of calories increased lean tissue development, as shown by muscle growth, over the standard diet. It has been calculated that for a 60 kg human, an effective amount of pyruvate can range from 0.01 gms to 0.17 gm per kilogram of body weight. For the 60 kg human, this converts to about 0.6 to 10 grams per day of pyruvate.

EXAMPLE IV

Pyruvyl-Creatine

An experiment similar to Example 3 is conducted except that pyruvyl-creatine is used in place of the calcium pyruvate. The results of this experiment will demonstrate that while a 30% increase in muscle tissue occurred, an overall weight gain of 10% occurs with the pyruvyl-creatine.

In one preferred embodiment of the present invention, there is provided a container or package containing a pharmaceutically acceptable mixture of pyruvate according to the invention in a unit dosage quantity (i.e., pills or capsules) together with instructions for anaerobic exercise. In another embodiment, the pyruvate composition of this invention is in combination with a liquid or powdered base, such as glucose, flavoring agents or carbohydrates to improve patient acceptance of the composition. The composition of this invention may also be incorporated as an ingredient in a foodstuff such as cookies, pretzels, candies, chewing gums, rehydration solutions and the like.

Industrial Applicability

The medical community and the serious athlete are constantly searching for compositions and methods that will enhance athletic performance and/or endurance while also increasing, the muscle mass of the athlete. There is also a need for nutritional compositions that will assist the catabolic patient in maintaining weight or preventing further weight loss and for compositions which increase the amount of muscle tissue in a mammal and reduce the catabolic effects of strenuous exercise. The present invention is based in part on the discovery that anaerobic exercise and the administration of calcium pyruvate and/or potassium pyruvate surprisingly produces outstanding increases in athletic endurance and performance while also increasing the muscle mass of the mammal. The present invention will be of substantial benefit to all athletes. especially body builders, weight lifters, football players and the like.

Although the invention has been described in connection with certain specific embodiments, it will be readily apparent to those skilled in the art that various changes can be made to suit specific requirements without departing from the spirit of and scope of the invention.

I claim as my invention:

1. A composition for enteral administration comprising calcium pyruvate and potassium pyruvate.

2. The composition according to claim 1 which additionally comprises pyruvyl-creatine.

3. The composition according to claim 1 wherein the weight ratio of calcium pyruvate to potassium pyruvate ranges from 1:10 to 10:1.

4. The composition according to claim 1 wherein the weight ratio of said pyruvyl-creatine to the sum of said calcium pyruvate and potassium pyruvate ranges from 10:1 to 1:1.

5. The composition according to claim 1 wherein said composition is in the form of a powder, tablet, capsule, pill, liquid, food additive, candy or confection.

6. The composition according to claim 5 wherein said powder is admixed with a liquid.

7. A method for enhancing the muscle mass of a mammal said method comprising administering to said mammal a therapeutically effective amount of pyruvate.

8. The method according to claim 7 wherein said pyruvate is selected from the group consisting of calcium pyruvate, magnesium pyruvate, potassium pyruvate, pyruvyl-creatine, pyruvyl-glycine, pyruvamides, pyruvyl-alanine, pyruvyl-glutamine, pyruvyl-tyrosine, pyruvyl-leucine, pyruvyl-valine, pyruvyl-isoleucine, pyruvyl-phenylalanine, pyruvyl-proline, pyruvyl-sarcosine, their amides, esters and salts and mixtures thereof.

9. The method according to claim 8 wherein said pyruvate comprises a mixture of calcium pyruvate, potassium pyruvate and pyruvyl-creatine.

10. The method according to claim 9 wherein the weight ratio of said calcium pyruvate to said potassium pyruvate ranges from 1:10 to 10:1.

11. The method according to claim 9 wherein the weight ratio of said pyruvyl-creatine to the sum of said calcium pyruvate and said potassium pyruvate ranges from 10:1 to 1:1.

12. The method according to claim 7 wherein said pyruvate is in the form of a powder, tablet, capsule, pill, liquid, food additive, candy or confection.

13. The method according to claim 12 wherein said powder is admixed with a liquid.

14. A method for increasing the muscle mass in a mammal which comprises the steps of:

1) administering orally to a mammal in need thereof, a therapeutically effective amount of pyruvate; and 2) subjecting said mammal to at least 20 minutes of anaerobic exercise per day.

15. The method according to claim 14 wherein said pyruvate is selected from the group consisting of calcium pyruvate, magnesium pyruvate, potassium pyruvate, pyruvyl-creatine, pyruvyl-glycine, pyruvamides, pyruvyl-alanine, pyruvyl-tyrosine, pyruvyl-glutamine, pyruvyl-leucine, pyruvyl-valine, pyruvyl-isoleucine, pyruvyl-isoleucine, pyruvyl-phenylalanine, pyruvyl-proline, pyruvyl-sarcosine, their amides, esters and salts and mixtures thereof.

16. The method according to claim 14 wherein said pyruvate comprises a mixture of calcium pyruvate and potassium pyruvate.

17. The method according to claim 16 wherein the weight ratio of calcium pyruvate to potassium pyruvate ranges from 10:1 to 1:10.

18. The method according to claim 16 wherein said pyruvate additionally comprises pyruvyl-creatine.

19. The method according to claim 16 wherein said composition is in the form of powder, tablet, capsule, pill, liquid, food additive, candy or confection.

20. The method according to claim 19 wherein said powder is admixed with a liquid,.

21. The method according to claim 14 wherein said pyruvate is selected from magnesium pyruvate, potassium pyruvate, pyruvyl-creatine, calcium pyruvate and mixtures thereof, and wherein said therapeutically effective amount ranges from 1.6 to 10 grams per day.

22. A method for increasing the muscle mass in a human, said method comprising the steps of:

a) enterally administering to said human at least from 1.6 to 10 grams per day of pyruvate anion; and b) subjecting said human to at least 20 minutes of anaerobic exercise per day.

23. The method of claim 22 wherein said pyruvate comprises a mixture of calcium pyruvate and potassium pyruvate.

24. The method of claim 23 wherein said pyruvate additionally comprises pyruvyl-creatine.

* * * * *